United States Patent [19]
Williams

[11] Patent Number: 5,941,830
[45] Date of Patent: Aug. 24, 1999

[54] SYSTEM AND METHOD FOR OPTIMAL SENSING OF CARDIAC EVENTS

[75] Inventor: Michael O. Williams, Mt. Shasta, Calif.

[73] Assignee: Pacesetter, Inc., Sunnyvale, Calif.

[21] Appl. No.: 09/049,786

[22] Filed: Mar. 27, 1998

[51] Int. Cl.$^6$ .................................................... A61B 5/04
[52] U.S. Cl. ................................. 600/509; 607/9; 607/5
[58] Field of Search .................................. 600/509, 510, 600/516, 521; 607/4, 5, 9, 25

[56] References Cited

U.S. PATENT DOCUMENTS

| | | | |
|---|---|---|---|
| 4,712,555 | 12/1987 | Thornander et al. . | |
| 4,762,136 | 8/1988 | Baker, Jr. . | |
| 5,348,021 | 9/1994 | Adams et al. | 600/521 |
| 5,458,115 | 10/1995 | Sivard et al. | 600/521 |
| 5,578,063 | 11/1996 | Bocek et al. . | |
| 5,632,267 | 5/1997 | Högnelid et al. . | |

OTHER PUBLICATIONS

Sutton, Richard And Bourgeois, Ivan; "The Foundations of Cardiac Pacing" vol. 1, Part 1; 1991; pp. 45–72.

*Primary Examiner*—William E. Kamm
*Assistant Examiner*—George R. Evanisko
*Attorney, Agent, or Firm*—Steven M. Mitchell

[57] ABSTRACT

A system and method for optimal sensing of cardiac events includes registering electrical activity from a cardiac event in a patient's heart and entering a refractory period after the cardiac event has been registered. The system and method further includes detecting when the electrical activity from the cardiac event has settled into a baseline region for a predetermined period of time, whereby the refractory period is ended at such time. The method may also implement a minimum backup timer and a maximum backup timer, which are set to predetermined minimum and maximum time periods, respectively, when the refractory period begins. In this case, the system ends the refractory period, either: (1) when the electrical activity settles into a baseline region for a predetermined period of time and the minimum time period elapses, or (2) when the maximum time period elapses, whichever occurs first. The method for controlling the length of the refractory period can be used to control sensing, pacing and defibrillator systems.

19 Claims, 8 Drawing Sheets

SYSTEM AND METHOD FOR OPTIMAL SENSING OF CARDIAC EVENTS

BACKGROUND OF THE INVENTION

1. Field of the Invention

The present invention relates to a system and method for optimal sensing of cardiac events. In particular, the present invention relates to a system and method for controlling a refractory period for a cardiac monitoring or therapy device to achieve optimal sensing of cardiac events.

2. Related Art

The system and method of the present invention are intended to be incorporated into a conventional pacemaker or defibrillator. Both devices are described below. A modern implantable defibrillator includes a pulse generator, which is connected to a patient's heart, via an electrode lead system having one or more electrode leads respectively carrying one or more electrodes. The pulse generator supplies stimulation pulses to the heart and is controlled by a control unit. A detector is arranged to sense heart activity via the electrode lead system, and to send detected information to the control unit for controlling the pulse generator in accordance therewith. An electrode switching unit is devised to connect different combinations of electrodes of the leads of the electrode lead system to the pulse generator according to a defined pattern or in some optional way. A conventional defibrillator senses when a heart is undergoing fibrillation and delivers a defibrillation shock to the heart. Defibrillators can also deliver tachyarrhythmia pacing therapy to the heart, known as antitachycardia pacing. This pacing consists of delivery of a train of pace pulses to the heart.

The operation of such a conventional defibrillator is described in detail in U.S. Pat. No. 5,007,422 to Pless et al. And in U.S. Pat. No. 5,632,267 to Högnelid et al. which are both incorporated herein, in their entirety, by reference.

Similarly, modern pacemakers include a pulse generator, which is connected to a patient's heart via an lead system having one or more leads with one or more electrodes. Typically, the leads are bipolar where localized sensing is required. The pulse generator provides pacing pulses to the heart and is controlled by a control unit. A detector is used to sense heart activity to control the pulse generator. Pacemakers traditionally delivery bradycardia pacing pulses to the heart. Antitachycardia pacing pulses are typically delivered at a much higher rate than bradycardia pacing pulses.

Modem pacemakers may include complex stimulation pulse generators as well as cardiac event sensors that can pace or sense in the atrium, the ventricle, or both the atrium and ventricle of the heart. Further, such pacemakers include telemetry capabilities so that the activity of the heart and pacemaker can be transmitted to an attending physician or cardiologist. Advantageously, such pacemakers are also programmable so that the same telemetry capabilities can be used by the attending physician or cardiologist in order to adjust the pulse characteristics such as width and voltage, and parameters associated with operation of the pacemaker. Such parameters not only influence the rate at which the pacemaker's stimulation pulses are generated, but also control the pacemaker's basic mode of operation, i.e., the heart chamber that is paced, as well as the heart chamber that is sensed. Hence, modern pacemakers offer great versatility in the manner of their use.

Figure 8:
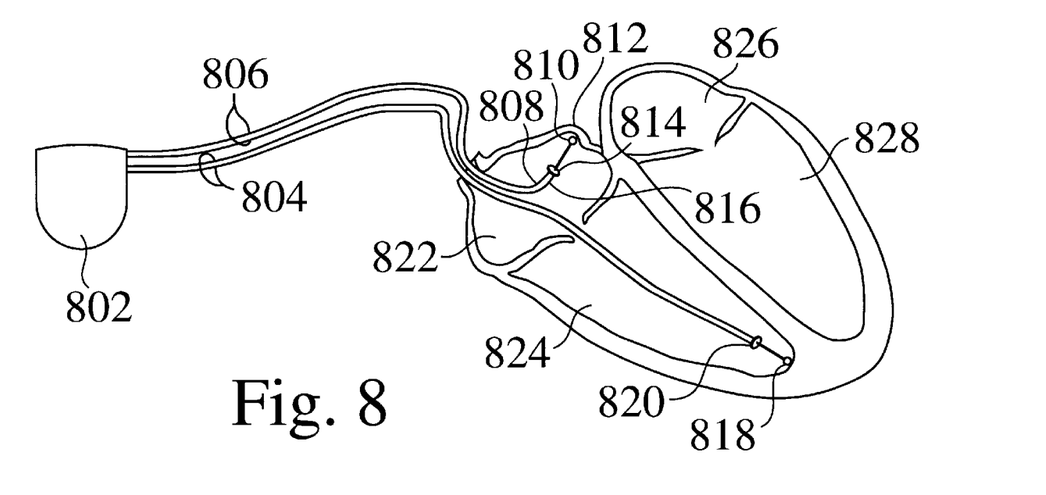
FIG. 8 is a simplified representation of the heart showing the manner in which a pacemaker is connected thereto through insertion of bipolar leads into both the right atrium and right ventricle.

Referring to FIG. 8, there is shown a simplified representation of one way that an implanted pacemaker 802 may make electrical contact with the heart. It is well known in the art that there are other ways to connect pacemakers to the heart. Further, the method for implanting leads for an implantable defibrillator is also well known in the art.

FIG. 8 shows the four (4) chambers of the heart, namely, the right atrium 822, the right ventricle 824, the left atrium 826, and the left ventricle 828. The atrium chambers function primarily as reservoirs into which incoming blood is received. The ventricles function primarily as pumping chambers to pump the blood away from the heart to a specific destination.

Right atrium 822 has an S-A node (not shown) that begins the electrical impulse that spreads in wave fashion to stimulate both right atrium 822 and left atrium 826. It is this electrical impulse that causes depolarization of the muscle tissue that forms the walls of the atria, thereby causing atrial contraction to occur. Right atrium 822 also includes an A-V node (not shown) which is stimulated by the electrical impulse propagated from the S-A node. Upon stimulation, and after a short pause (typically about 0.1 seconds), the A-V node initiates an electrical impulse that starts traveling down an A-V bundle (not shown). This A-V bundle branches and distributes the electrical impulse throughout the myocardium or heart muscle, thereby causing the ventricles to depolarize and contract.

FIG. 8 depicts the use of two (2) bipolar leads 804 and 806, each being directed into a separate chamber of the heart. A bipolar lead comprises a single filar strand that includes two (2) electrically insulated conductors. For example, lead 806 includes a first conductor 808 that is electrically connected to a distal tip 810 of the lead. Distal tip 810 is typically placed in a cavity of right atrium 822 referred to as an atrial appendage 812. At a known distance from distal tip 810, an electrode ring 814 is electrically connected to another conductor 816 of bipolar lead 806. Similarly, a distal tip 818 and a conductive ring 820 are associated with bipolar lead 804 which is placed in the apex of right ventricle 824. The manner in which leads 804 and 806 are inserted into the heart, as well as the manner in which pacemaker 802 is implanted in the body of a patient, are well known in the art.

With every natural or intrinsic heart activity, an electrogram can be detected by the pulse generator via the lead. In the waveform of the electrogram, one can identify the intrinsic deflection, a rapid biphasic voltage change, corresponding to the depolarization wave front passing under the electrode(s). In the waveform of the electrogram, there are several other components which are sometimes seen in addition to the intrinsic deflection, including repolarization potentials, QRS in the atrial electrogram, myopotentials in the unipolar pacing system (generated by skeletal-muscle contraction), and electromagnetic interference. The intrinsic deflection is the most important component of natural heart activity detected by the electrode(s).

Figure 9:
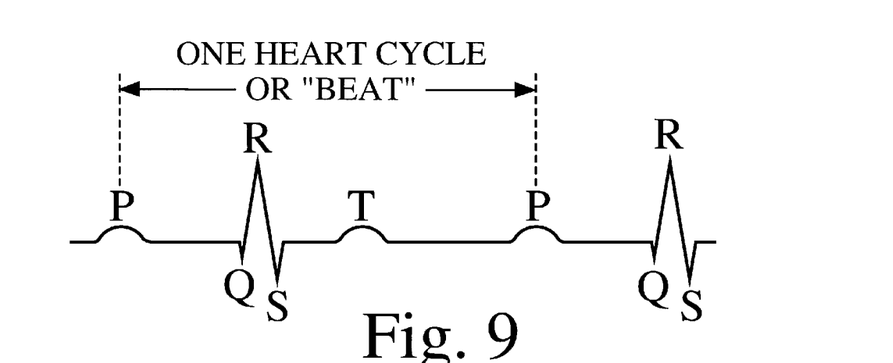
FIG. 9 is a timing diagram illustrating the normal, non-paced operation of the heart as sensed through conventional skin ECG electrodes or equivalent.

FIG. 9 shows a representation of the various waveforms that are generated, as sensed by skin electrodes placed on the chest. A P-wave represents the depolarization of both atria. The QRS-wave, commonly referred as the QRS complex, represents the electrical impulse as it travels from the A-V node to the various fibers branching from the left and right bundle branches as it is distributed into the myocardial cells, thereby causing ventricular depolarization. The T-wave represents the repolarization of the ventricles so that they may be stimulated again. Repolarization of the atrium is usually not sensed because it occurs about the same time as the QRS complex, and any signals representative of atrial repolarization are therefore masked out by the QRS complex.

One cardiac cycle is represented by a P-wave, a QRS complex, and a T-wave. This cardiac cycle is repeated continuously as the heart pumps blood. In summary, the P-wave represents depolarization of the atria. The QRS complex, sometimes referred to as simply an R-wave, represents the depolarization of the ventricles. Depolarization/contraction of the atria, followed a short time thereafter by depolarization/contraction of the ventricles, are the cardiac events that must occur if the heart is to efficiently perform its function as a pump in distributing blood throughout the body.

Returning now to a discussion of pacemakers, there are two types of pacemakers, fixed or asynchronous pacemakers and demand pacemakers. In an asynchronous or fixed rate pacemaker system, the control unit acts like a counter, which counts down, for example, every millisecond (ms). When the counter reaches zero, it commands an output circuit to deliver an electrical stimulus to the heart muscle. At the same time, the stimulus resets the counter to its original value. The time between two electrical impulses is referred to as an escape interval. The escape interval corresponds to the paced heart rate or basic rate. The escape interval is determined by the value to which the counter is set. In the fixed rate system, electrical stimuli arrive at fixed intervals, irrespective of natural or intrinsic heart activity.

An asynchronous pacemaker competes with a patient's natural heart activity and can sometimes stimulate the heart in a vulnerable period which could induce arrhythmias. However, if the counter is reset at the moment of spontaneous cardiac activity, competition between the pacemaker and the natural heart rhythm will be avoided. As such, demand pacemakers having the ability to sense intrinsic heart activity have been developed.

A demand pacemaker uses a sensing amplifier to detect intrinsic heart activity, so that the pacemaker delivers an electrical stimulus, also referred to herein as a pace pulse, to the heart only when the natural heart rate drops below the rate set by the counter. Thus, if the pacemaker does not detect intrinsic heart activity by the time the counter reaches zero, the pacemaker will deliver an electrical stimulus to the heart. The demand pacemaker ensures that the lowest possible heart rate is the basic rate of the pulse generator. This rate is sometimes referred to as the lower rate or backup rate. If the pulse generator is inhibited from delivering an electrical stimulus to the heart, because the sensing amplifier senses intrinsic heart activity, the counter is reset and a new escape interval begins. Similarly, if no intrinsic heart activity has been detected, and the pulse generator delivers an electrical stimulus to the heart, the counter is reset at the same time as delivery of the stimulus.

In a demand pacemaker, wherein a stimulating pulse is provided by the pacemaker only when a natural cardiac event fails to occur within a prescribed escape time interval, the escape time interval can be adjusted as a function of the reference interval measurement, and thereby adjust the pacing rate as a function of physiological need, as shown in U.S. Pat. No. 4,712,555 to Thornander et al.

In a demand pacemaker it is common to define an escape interval during which activity within the heart is sensed. If a natural cardiac event occurs during this escape interval, that is if a natural P-wave or R-wave is sensed, then a corresponding stimulating pulse need not be generated. This mode of operation allows the heart to function in its natural state, if it is able. Further, a demand pacemaker helps conserve the limited power stored within the battery of the pacemaker. One problem with asynchronous pacemakers is that they cannot change the stimulation pattern. The asynchronous pacemaker is set to a fixed rate and is refractory to intrinsic cardiac activity throughout its cycle.

In demand pacemakers and in defibrillators, both having sensing capabilities, signals such as interference, repolarization signals, and other far field signals may appear to the pulse generator to be intrinsic cardiac events, thereby causing the pulse generator to reset the counter. However, there is a certain period after heart activity during which new heart activity cannot physiologically occur. During this period, any cardiac event sensed by the pulse generator cannot correspond to new cardiac activity, and as such, the pacemaker counter should not be reset and a defibrillation shock should not be applied. This period is called the "refractory period" of the pulse generator.

The nominal refractory period for conventional pacemakers starts either with sensing of an intrinsic cardiac event or delivery of a pace pulse, and generally lasts for approximately 300 to 350 ms following delivery of a pace pulse or approximately 130 to 150 ms following sensing of an intrinsic cardiac event. The nominal refractory period for a defibrillator starts with delivery of a defibrillation shock to the heart, and generally lasts approximately 500 to 1000 ms.

In a defibrillator, the pulse generator is trying to detect very fast heart rates, greater than 300 beats per minute. As such, the pulse generator must be alert as much as possible. Using a fixed refractory period limits the fastest heart rate that can be sensed. Thus, there is a need to minimize the refractory period as much as possible.

A pacemaker typically operates at approximately 70–100 beats per minute, much slower than the rate of a heart in fibrillation. In this case, if the refractory period is too long, it generally does not pose a problem. However, if the refractory period is too short, then oversensing occurs, and necessary pacing pulses may not be delivered to the heart. As such, there is a need to monitor the cardiac event so that the refractory period does not end prior to the end of cardiac event. This prevents the same cardiac event from being sensed more than once.

The simple approach of programming refractory periods to a fixed length of time can lead to refractory periods which are longer than necessary, thus wasting valuable sensing opportunities. Alternatively, the approach may lead to refractory periods which are shorter than necessary, leading to multiple sensing of a single cardiac event. What is needed is a method for setting the refractory period such that the refractory period ends when the cardiac activity has ceased.

SUMMARY OF THE INVENTION

The present invention prescribes a method for determining the length of refractory periods in pacemakers, defibrillators and similar devices based on what is needed, rather than a fixed length of time. In particular, the refractory period is ended as soon as the electrical activity associated with a cardiac event has finished. This method allows for better sensing by expanding the alert period of the device to the maximum time possible and helps prevent oversensing of paced or intrinsic cardiac events.

The apparatus of the invention includes a pulse generator and a lead. The lead has electrodes which are attached to the myocardium. The pulse generator has a sensing amplifier to sense an intrinsic cardiac event and has means to deliver a defibrillation shock or a pace pulse to the heart. Once the pulse generator registers a cardiac event (e.g., senses a cardiac event or delivers an electrical pulse to the heart), the pulse generator enters a refractory period. During this period, the pulse generator monitors the output from the heart to detect when the electrical activity from the cardiac event has ceased. In particular, the pulse generator looks to see when the electrical activity has remained within a baseline region for a predetermined length of time. Once this occurs, the pulse generator ends the refractory period. This method ensures that the cardiac event has finished and monitoring of the heart may be reinitiated without fear of oversensing.

Because the task of a defibrillator is to detect very fast heart rates, greater than 300 beats per minute, the pulse generator must be alert as much as possible. Thus, there is a need to minimize the sense refractory period, including that following a defibrillation shock, as much as possible. The conventional intra cardiac electrogram sensing, the refractory period is set a fixed length of, for example, 135 ms. The nominal refractory period for a conventional defibrillator is typically 500 to 1000 ms. This fixed refractory period limits the fastest heart rate that can be sensed. The present invention dynamically alters the length of the refractory period so that it ends when the electrical activity associated with the cardiac event has ceased. Thus, the present invention minimizes the length of the refractory period to optimize the sensing capabilities of the defibrillator.

A pacemaker typically operates at approximately 70–100 beats per minute, much slower than the rate of a heart in fibrillation. In this case, if the refractory period is too long, it generally does not pose a problem. However, if the refractory period is too short, then oversensing occurs, and necessary pacing pulses may not be delivered to the heart. The present invention monitors the electrical activity from the cardiac event so that the refractory period does not end prior to the end of cardiac event. This prevents the same cardiac event from being sensed more than once.

The present invention also employs a backup limit, controlled by a timer, which sets minimum and maximum time limits for the refractory period. If the electrical activity associated with a cardiac event ends prior to the end of the minimum backup timer, the pulse generator will not end the refractory period. Instead, it will continue in the refractory period until at least the minimum time period has elapsed.

Similarly, the maximum backup timer may be used to prevent the refractory period from lasting too long. For example, when noise or low amplitude cardiac activity is present outside of the baseline region, there is constant activity outside of the baseline region. In this case, the electrical activity never settles into a baseline region for a predetermined period of time. Thus, the refractory period ends up being set to a fixed, maximum time period, as controlled by the maximum backup timer. This maximum backup timer period may be varied to accommodate paced and sensed cardiac events and defibrillation therapy.

BRIEF DESCRIPTION OF THE FIGURES

The foregoing and other features and advantages of the invention will be apparent from the following, more particular description of a preferred embodiment of the invention, as illustrated in the accompanying drawings.

DETAILED DESCRIPTION OF THE PREFERRED EMBODIMENTS

A preferred embodiment of the present invention is now described with reference to the figures where like reference numbers indicate identical or functionally similar elements. Also in the figures, the left most digit of each reference number corresponds to the figure in which the reference number is first used. While specific configurations and arrangements are discussed, it should be understood that this is done for illustrative purposes only. A person skilled in the relevant art will recognize that other configurations and arrangements can be used without departing from the spirit and scope of the invention.

It would be apparent to one skilled in the relevant art that other systems could also be used to implement the method of the present invention to control the refractory period. The method of the present invention is described for use in demand pacemakers and defibrillators. This description is presented by way of example. It is intended that the method of the present invention can also be implemented to control refractory periods in cardiac monitors, ECG and intracardiac ECG interpretation algorithms, automatic external defibrillators, external pacemakers and other similar devices, as would be apparent to one skilled in the relevant art. Further, although the method of the present invention is discussed within the context of an implantable lead system, it would be apparent to one skilled in the relevant art that this method could also be used to control the refractory period for a system using surface electrodes.

Figure 1:
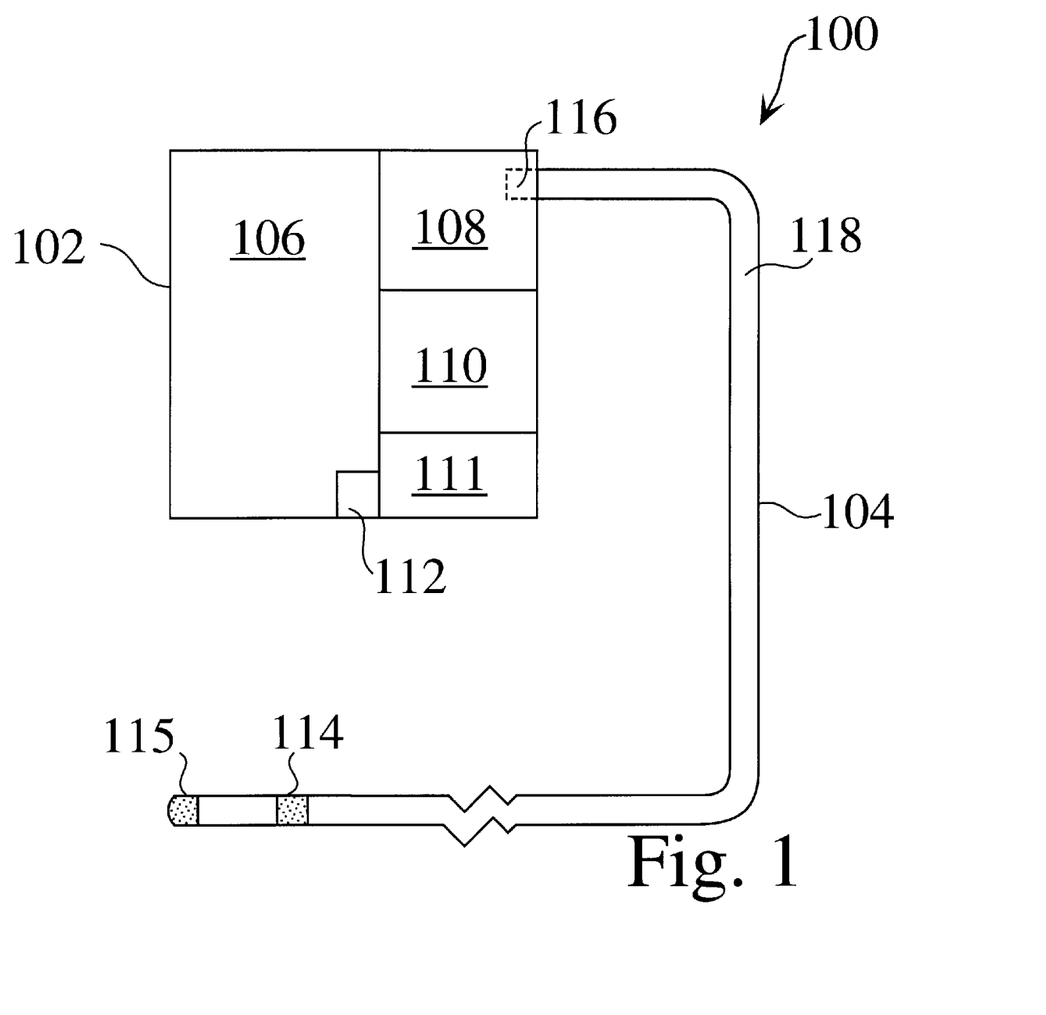
FIG. 1 shows a system for implementing the method of the present invention.

FIG. 1 shows a high-level, exemplary block diagram of a sensing and stimulation system 100 that can be used for implementing the present invention. System 100 includes a pulse generator 102 and a lead 104 and can be used for sensing, pacing, and/or defibrillation. Pulse generator 102 consists of a power source 106, such as a battery, an electrical impulse former, e.g., an output circuit 108, a timing control circuit 110, and a sensing circuit 111. The configuration and circuitry for implementing pulse generator 102 would be apparent to one skilled in the relevant art having benefit of this disclosure. Conventional sensing of the R-wave using a bipolar lead can be instituted using the method described in U.S. Pat. No. 4,712,555 to Thornander et al., entitled "Physiologically Responsive Pacemaker and Method of Adjusting the Pacing Interval Thereof," which is incorporated in its entirety herein by reference.

Lead 104 connects ring electrode 114 and tip electrode 115 to pulse generator 102 via a connector pin 116. Electrodes 114 and 115 and connector pin 116 are connected by an insulated wire referred to as a lead body 118. In one embodiment, lead 104 is fixed to the wall of the patient's heart, using a fixation device as would be apparent to one skilled in the relevant art, so that it remains in contact with the myocardium. It will also be understood that for atrial sensing the lead may not be fixed to the myocardium.

Figure 2A:
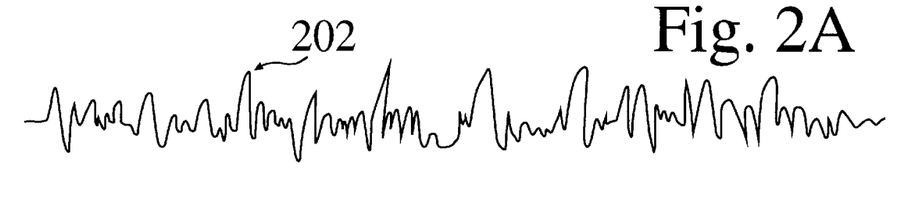
FIGS. 2A and 2B show electrical stimuli of a conventional defibrillator.
Figure 2B:
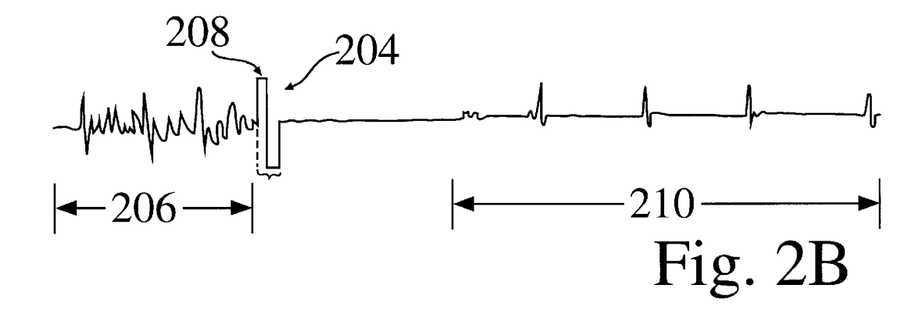

FIGS. 2A and 2B show electrical activity of a heart undergoing fibrillation and the resulting electrical stimuli from a defibrillator. Waveform 202, in FIG. 2A, shows electrical activity of the heart undergoing fibrillation. Fibrillation is classically defined as an irregularly irregular heartbeat with a cycle length from 80–300 ms.

Waveform 204, in FIG. 2B, shows electrical activity of the heart with ventricular fibrillation (VF) therapy. An area marked as 206 on the left side of waveform 204, shows the heart in fibrillation, similar to waveform 202. A defibrillation shock 208 is then applied to the heart. Defibrillation shock 208 generally lasts 5–15 ms.

An area marked as 210, to the right side of shock 208, shows the heart returning to a normal heartbeat after application of the ventricular fibrillation therapy. The unmarked area between shock 208 and area 210 represents the period of time after delivery of a defibrillation shock during which the heart recovers from the shock therapy. This time period is typically 500 to 1000 ms.

In the example shown in FIG. 2B, the heart is monitored after application of defibrillation shock 208 to detect subsequent cardiac 4 activity. This is to determine if the heart is still in fibrillation such that an additional defibrillation shock needs to be applied. If the refractory period following delivery of the defibrillation shock is too long, then the sensing mechanism, generally a pulse generator, may miss sensing certain cardiac activity that would provide the necessary information to make a rapid diagnosis if additional therapy is required. Thus, the longer the refractory period, the greater the chance that some heartbeats may not be sensed.

If the refractory period following delivery of a defibrillation shock is too short, then pulse generator 102 may sense electrical activity resulting from recovery of the heart from the defibrillation shock. This electrical activity may result in the device misdiagnosing the condition of the patient's heart (e.g., mistakenly thinking that the heart is still in fibrillation.) The device may then unnecessarily deliver additional ventricular fibrillation therapy to the heart.

Figure 3A:
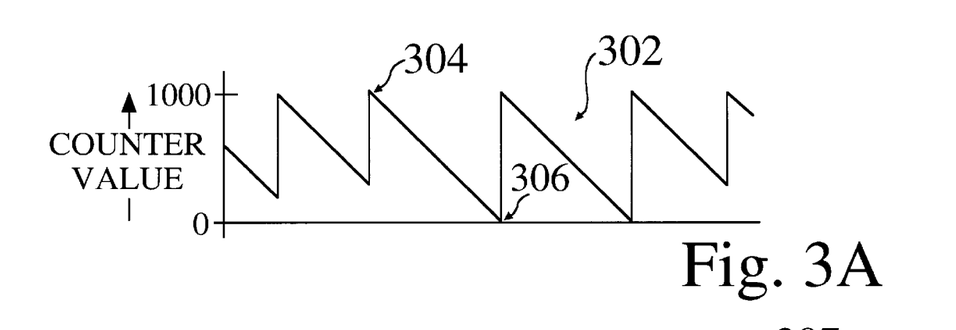
FIGS. 3A–3C show electrical stimuli of a conventional demand pacemaker for both inhibited and triggered pulse generators.
Figure 3B:
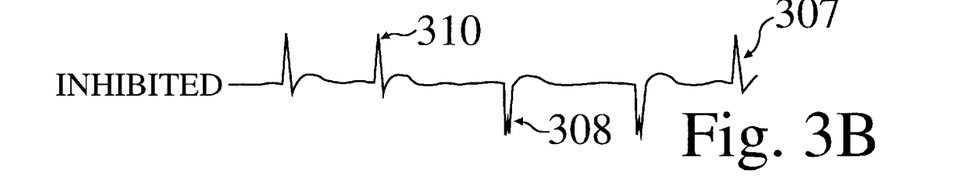
Figure 3C:
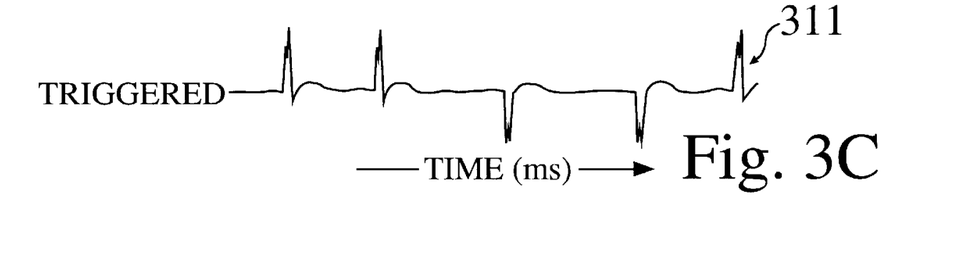

FIGS. 3A–3C show electrical activity of the heart associated with a demand pacemaker. Waveform 302, in FIG. 3A, represents the counter of timing control circuit 110. In a demand pacemaker, the counter is reset when pulse generator 102 senses intrinsic cardiac activity. For example, the counter is shown being reset corresponding to a point 304 on waveform 302 which represents intrinsic cardiac activity. The counter is also reset if pulse generator 102 does not detect intrinsic cardiac activity prior to the point when the counter reaches zero, as shown at a point 306 on waveform 302. At point 306, pulse generator 102 delivers a pace pulse to the heart, and resets the counter.

FIG. 3B shows an inhibited example of a demand pacemaker. In this example, pulse generator 102 delivers a pace pulse, such as shown at a point 308 in a waveform 307, only when the counter reaches zero. If intrinsic cardiac activity, as shown at a point 310, is detected, pulse generator 102 is inhibited from delivering a pace pulse, and the counter is reset.

FIG. 3C shows a triggered example of a demand pacemaker. In this example, as illustrated by a waveform 311, pulse generator 102 delivers a pace pulse when spontaneous cardiac activity is detected or when the counter reaches zero. The counter is reset after each delivered pulse. The present invention can be used to control the refractory period of a demand pacemaker, either in the inhibited or triggered examples.

In the examples shown in FIGS. 3B and 3C, if the refractory period, following sensing of intrinsic cardiac activity or delivery of a pace pulse, is too short (i.e., shorter than the duration of the cardiac event), then pulse generator 102 will sense the same cardiac event more than once, resulting in the counter for the escape interval being reset prematurely. Further, in the triggered example, premature sensing of the same cardiac event will result in pacing pulses not being appropriately delivered to the heart. If the refractory period is set for a fixed period of time which is less than the escape interval and longer than the duration of the sensed cardiac event, there may be a period of time after the cardiac event has ended, during which pulse generator 102 is still in the refractory period, resulting in undersensing of a patient's heart activity.

The present invention dynamically alters the refractory period so that the refractory period ends when the electrical activity from the registered cardiac event ceases. A cardiac event can be "registered" if pulse generator 102 senses an intrinsic cardiac event, delivers a pace pulse to the heart, or delivers a defibrillation shock to the heart.

Figure 4:
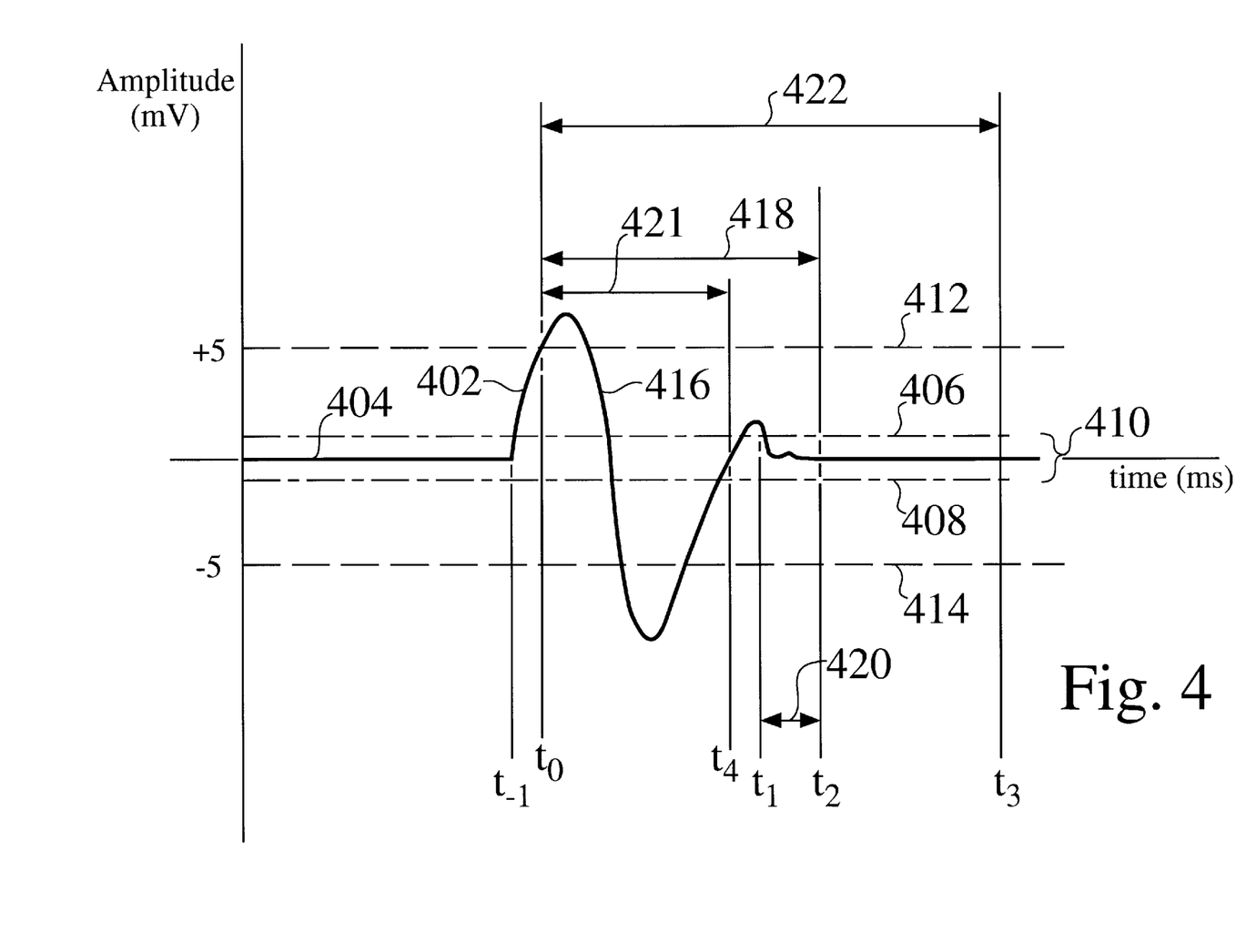
FIG. 4 is a graph of the present invention as applied to a natural intrinsic cardiac event.

FIG. 4 is a graph showing the present invention as implemented with respect to an intrinsic cardiac event 402. The present invention is also intended to be used to control refractory periods following delivery of a pacing pulse, including both antitachycardia and bradycardia pacing pulses, or delivery of a defibrillation shock to the heart, as would be apparent to one skilled in the relevant art. The use of the present invention with respect to paced cardiac events and defibrillation therapy will be discussed in further detail below.

The graph shown in FIG. 4 includes an x-axis, representing time measured in milliseconds (ms) and a y-axis, representing amplitude of the signal, measured in millivolts (mV). A baseline 404 of the heart's electrical activity is shown in FIG. 4. Baseline 404 is indicated by the measurement of the heart's electrical activity between beats, i.e. at rest. As such, the baseline represents 0 mV of output, as shown in FIG. 4. The baseline is determined based on each individual patient's physiological characteristics.

Positive and negative baseline thresholds 406 and 408, respectively, represented by dotted-dashed lines, are also shown in FIG. 4. The area of the graph between positive and negative baseline thresholds 406 and 408 defines a baseline region 410. Baseline region 410 provides for minor variations in the heart's electrical activity, noise, and any imprecisions of the sensing equipment. In an embodiment in which the sensing lead is disposed in the ventricle, positive baseline threshold 406 is within the range of 0.1 to 1 mV and negative baseline threshold 408 is within the range of –0.1 to –1 mV. In an embodiment in which the sensing lead is disposed in the atrium, positive baseline threshold 406 is within the range of 0.05 to 0.5 mV and negative baseline threshold 408 is within the range of –0.05 to –0.5 mV. It would be apparent that these baseline thresholds may vary depending on the physiologic condition of the particular patient.

FIG. 4 also includes positive and negative sensing thresholds 412 and 414, respectively, represented by dashed lines. Sensing thresholds 412 and 414 are used to determine when cardiac activity has occurred, as described in further detail below. In the graph of FIG. 4, positive sensing threshold 412 is 5 mV and negative sensing threshold 414 is −5 mV. It would be apparent that these sensing thresholds may vary depending on the physiologic condition of the particular patient.

A sensed cardiac event includes a portion thereof commonly referred to the QRS complex, sometimes referred to simply as the R-wave. In FIG. 4, the R and S-wave portions of the QRS complex are referred to as an R-wave 416. R-wave 416 is shown on the graph as that portion of the signal between time $t_{-1}$ and time $t_1$. Pulse generator 102 senses that a cardiac event has occurred, and in particular, senses R-wave 416 of the cardiac event, once the signal passes either positive or negative sensing thresholds 412 and 414. In the signal shown in FIG. 4, R-wave 416 is first sensed as it passes positive sensing threshold 412 at a time to. In the case of a paced cardiac event, time to occurs when the pace pulse is delivered to the heart. In the case of a defibrillator, time to occurs when a defibrillation shock is delivered to the heart.

In the example of FIG. 4, pulse generator 102 registers cardiac event 402 and then enters into a refractory period 418, shown as the period between time $t_0$ and time $t_2$. During refractory period 418, pulse generator 102 assumes that all cardiac activity during the refractory period is associated with the cardiac event that initiated the refractory period. Thus, the refractory period is a means for bounding all cardiac activity associated with a single cardiac event. This prevents pulse generator 102 from sensing the same cardiac event twice.

During refractory period 418, pulse generator 102 senses the electrical signal from the heart and detects when the signal settles into baseline region 410 for a predetermined period of time 420. Time period 420 is shown in the graph as the period between time $t_1$ and time $t_2$. It would be apparent to one skilled in the relevant art that time period 420 could vary depending on the particular physiological characteristics of each individual patient. For example, time period 420 can range between 20 to 600 ms. At time $t_2$, indicating that the electrical activity has settled into baseline region 410 for time period 420, pulse generator 102 will end refractory period 418 and reinitiate sensing for a new cardiac event. As such, refractory period 418 varies depending on the length of time it takes the electrical activity to settle into baseline region 410 for time period 420.

The use of minimum and maximum backup timers is also shown in FIG. 4. The minimum backup timer insures that there is a minimum length for the refractory period. In most cases, this minimum backup timer will rarely be used, because the minimum backup timer is usually set to a time period shorter than the self-terminating refractory period. In particular, when R-wave 416 is sensed at time $t_0$, the microprocessor sets the minimum backup timer for a minimum predetermined period of time 421, ending at a time $t_4$, as shown in FIG. 4. In one embodiment, minimum time period 421 is within a range of 70 to 120 ms. It would be apparent to one skilled in the relevant art that the minimum backup timer could be set to various time periods depending on the particular physiological characteristics of each individual patient.

The maximum backup timer insures that if there is irregularity in the heart's electrical activity, or significant noise in the signal, or other problems with the sensing such that the signal does not stay within baseline region 410 for the predetermined period of time 420, that the maximum backup timer will signal the microprocessor to end the refractory period. In particular, when R-wave 416 is sensed at time to, the microprocessor sets the timer for a maximum predetermined period of time 422, ending at a time $t_3$, as shown in FIG. 4. In one embodiment, maximum time period 422 is within a range of 120 to 600 ms. It would be apparent to one skilled in the relevant art that the maximum backup timer could be set to various time periods depending on the particular physiological characteristics of each individual patient.

Similarly, for paced cardiac events minimum time period 421 can be within a range of 70 to 120 ms, and maximum time period 422 can be within a range of 120 to 600 ms. However, in the case of a paced cardiac event, the electrical activity resulting from delivery of a pace pulse typically lasts longer than electrical activity resulting from an intrinsic cardiac event. Thus, the maximum backup timer for a paced cardiac event can be set to a longer maximum time period 422 than for an intrinsic event, so that the maximum timer does not run out before the electrical activity settles into baseline region 410. Minimum time period 421 for the minimum backup timer and predetermined time period 420 may also be extended, accordingly. Similarly, the values for predetermined time period 420, minimum time period 421 and maximum time period 422 may be different for anti-tachycardia and bradycardia pace pulses, as would be apparent to one skilled in the relevant art.

In the case of a defibrillator, the electrical activity resulting from delivery of a defibrillation shock lasts longer than either cases of paced or intrinsic cardiac activity. As such, in one embodiment, the minimum time period for a defibrillator is within a range of 250 to 750 ms, and the maximum time period is within a range of 750 ms to 2 seconds. Similarly, predetermined time period 420 may also be adjusted accordingly, as would be apparent to one skilled in the relevant art.

Figure 5:
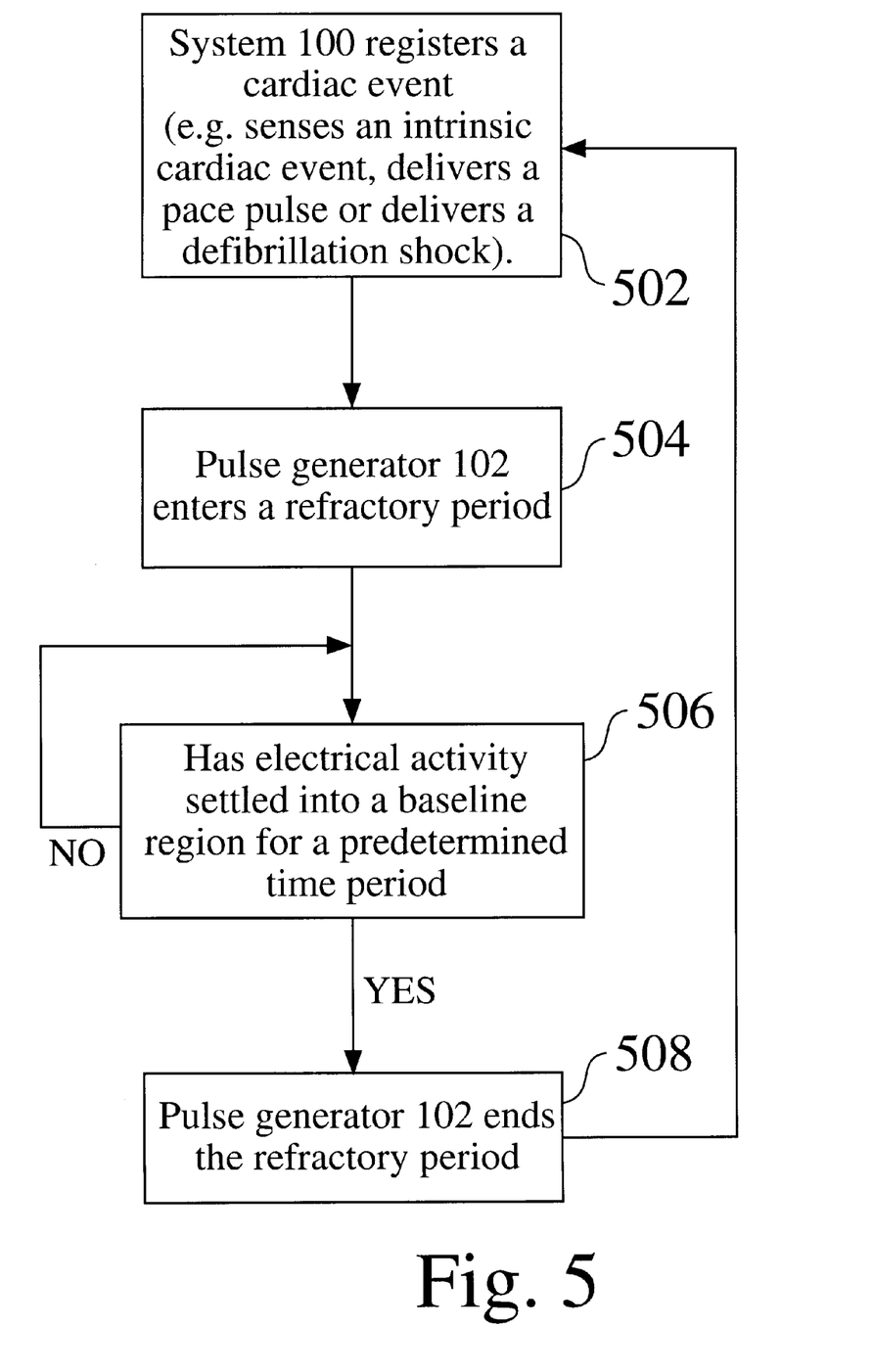
FIG. 5 is a high level flowchart showing a first method of the present invention.
Figure 6:
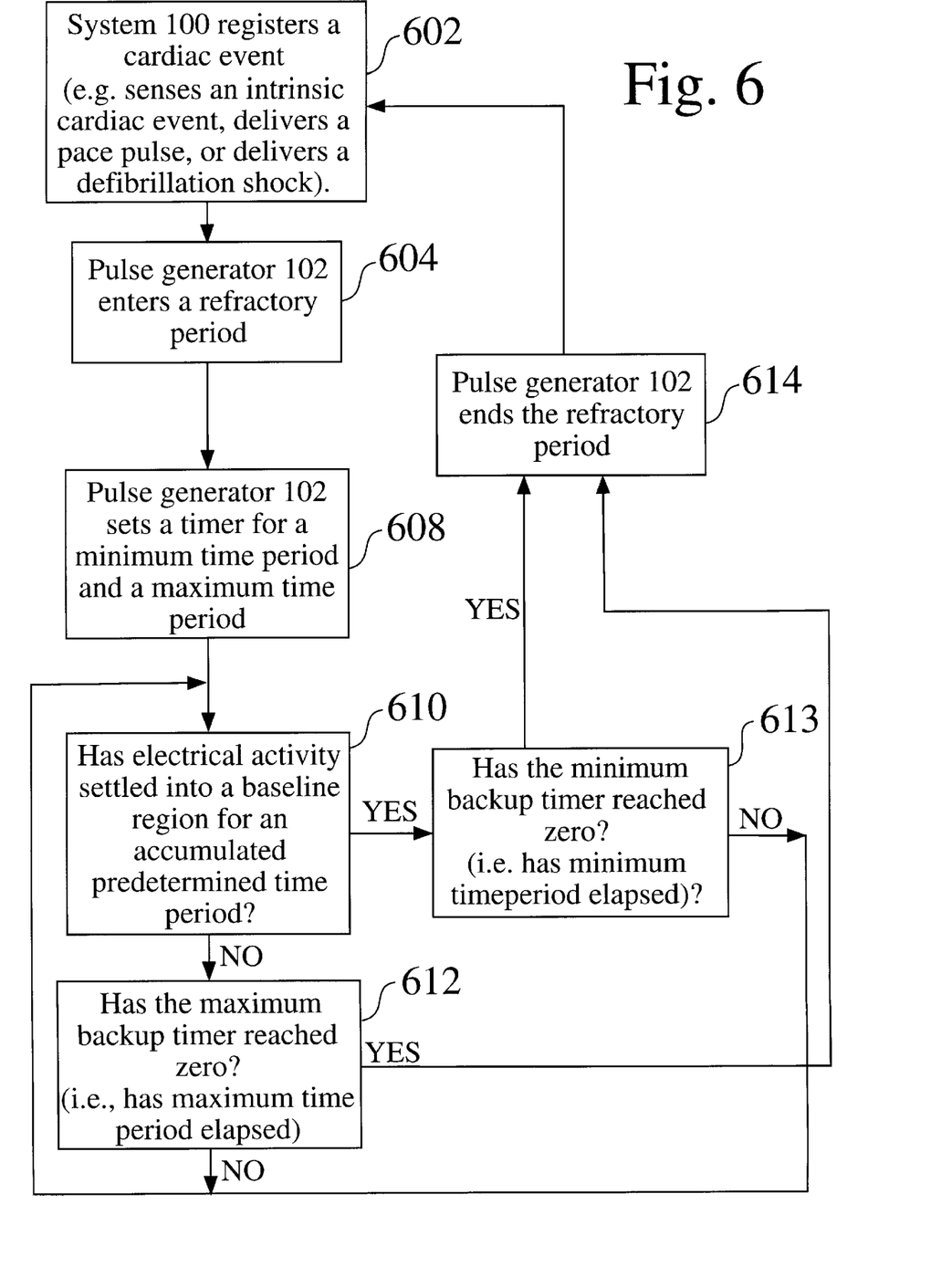
FIG. 6 is a high level flowchart showing a second method of the present invention.

FIGS. 5 and 6 show flowcharts of the method of the present invention. FIG. 5 shows the steps of the method of the present invention, without the use of backup timers. In this case, system 100 registers a cardiac event, such as detection of an intrinsic cardiac event, delivery of a pace pulse to the heart, or delivery of a defibrillation shock to the heart, as shown in a step 502.

When a cardiac event is registered, pulse generator 102 enters a refractory period, as shown in a step 504. During the refractory period, pulse generator 102 tracks the electrical activity from the cardiac event to detect when the cardiac event has settled into a baseline region for a predetermined time period. As shown in a step 506, if the cardiac event is outside of the baseline region, pulse generator 102 continues tracking. If the electrical activity from the cardiac event is within the baseline region for the predetermined period of time, pulse generator 102 ends the refractory period, as shown in a step 508, and system 100 continues sensing for the next occurrence of a cardiac event.

FIG. 6 shows the method of the present invention, including the use of minimum and maximum backup timers incorporated in the system. In this embodiment, system 100 registers electrical activity from the heart indicating the occurrence of cardiac event, as shown in a step 602. When the cardiac event is registered, pulse generator 102 enters a refractory period, as shown in a step 604. Further, when the cardiac event is registered, pulse generator 102 sets a timer for a minimum predetermined time period and a maximum predetermined time period, as shown in a step 608.

During the refractory period, pulse generator 102 tracks the electrical activity from the cardiac event to detect when the cardiac event has settled into a baseline region for a predetermined time period, as shown in a step 610. If the cardiac event is outside of the baseline region, the process moves to a step 612, in which pulse generator 102 checks to see if the maximum time period has elapsed. If the maximum backup timer has not reached zero, pulse generator 102 returns to step 610 to check the electrical activity from the cardiac event again. The process continues in this loop between steps 610 and 612, until one of the events in steps 610 or 612 occurs.

If the event in step 610 occurs, i.e., the electrical activity from the cardiac event is within the baseline region for the predetermined period of time, pulse generator 102 checks to see if the minimum time period has elapsed, as shown in a step 613. If the minimum time period has elapsed, pulse generator 102 ends the refractory period, as shown in a step 614, and system 100 continues sensing for the next occurrence of a cardiac event. If the minimum time period has not yet elapsed, pulse generator 102 returns to step 610 to check the electrical activity from the cardiac event again. The process continues in this loop between steps 610, 612 and 613, until one of the events in steps 610, 612 or 613 occurs.

If the event in step 612 occurs, i.e., the electrical activity from the cardiac event remains outside the baseline region, but the maximum time period elapses, pulse generator 102 will also end the refractory period, as shown in step 614. The method of the present invention, shown in FIGS. 5 and 6, provides a means to dynamically adjust the refractory period after the occurrence of a cardiac event, to more effectively monitor a patient's heart activity.

Figure 7:
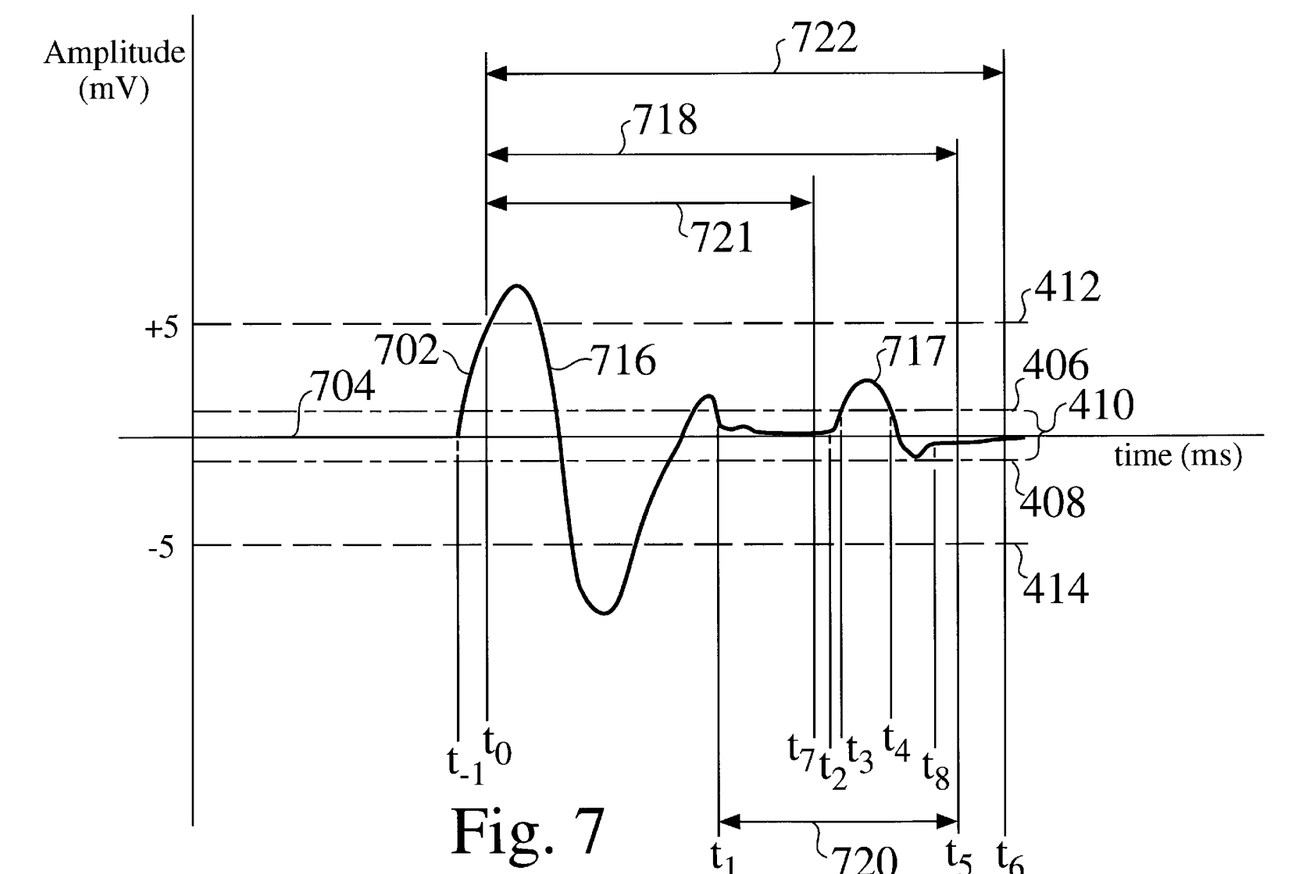
FIG. 7 is a graph of a second embodiment of the present invention as applied to a natural intrinsic cardiac event.

FIG. 7 is a graph of a second embodiment of the present invention as applied to an intrinsic cardiac event. The graph shown in FIG. 7 includes an x-axis, representing time measured in milliseconds (ms) and a y-axis, representing amplitude of the signal, measured in millivolts (mV). FIG. 7 shows both the R-wave and the T-wave of a cardiac event 702. The graph also includes a baseline 704 which indicates the measurement of the heart's electrical activity between beats, i.e. at rest. As such, baseline 704 represents 0 mV of output.

Similar to the graph shown in FIG. 4, positive and negative baseline thresholds 406 and 408, respectively, represented by dotted-dashed lines, are also shown in FIG. 7. The area of the graph between positive and negative baseline thresholds 406 and 408 defines baseline region 410.

FIG. 7 also includes positive and negative sensing thresholds 412 and 414, respectively, represented by dashed lines, as explained above with respect to FIG. 4.

As in FIG. 4, cardiac event 702 includes the R and S-wave portions of the QRS complex, referred to in this application as an R-wave 716. R-wave 716 is shown on the graph as that portion of the signal between time $t_{-1}$ and time $t_1$. Pulse generator 102 senses that a cardiac event has occurred, and in particular, senses R-wave 716 of the cardiac event, once the signal passes either positive or negative sensing thresholds 412 and 414. In the signal shown in FIG. 7, R-wave 716 is first sensed as it passes positive sensing threshold 412 at a time $t_0$. In the case of a paced cardiac event, time $t_0$ would occur when pulse generator 102 delivers a pace pulse to the heart and in a defibrillator, time $t_0$ would occur when pulse generator 102 delivers a defibrillation shock to the heart.

Cardiac event 702 also includes a portion commonly referred to as a T-wave 717. T-wave 717 is shown on the graph as that portion of the signal between time $t_2$ and time $t_8$. T-wave 717 is a portion of the electrical signal of cardiac event 702. Often, T-wave 717 passes outside baseline region 410, and depending on the physical characteristics of the patient, may also pass outside sensing thresholds 412 or 414. In order to avoid mistaking T-wave 717 for a new cardiac event, the present invention must be designed to continue the refractory period through the end of T-wave 717.

Once a cardiac event has been registered, pulse generator 102 enters into a refractory period 718, shown as the period between time $t_0$ and time $t_5$. During refractory period 718, pulse generator 102 assumes that all cardiac activity is associated with the cardiac event that initiated the refractory period. Thus, the refractory period is a means for bounding all cardiac activity associated with a single cardiac event. This prevents pulse generator 102 from sensing the same cardiac event twice.

During refractory period 718, pulse generator 102 senses the electrical signal from the heart and detects when the signal settles into baseline region 410 for a predetermined period of time 720. Time period 720 is shown in the graph as the period between time $t_1$ and time $t_5$. It would be apparent to one skilled in the relevant art that time period 720 could vary depending on the particular physiological characteristics of each individual patient. For example, time period 720 can range between 20 to 600 ms.

As shown in FIG. 7, T-wave 717 passes outside baseline region 410 at a time $t_3$ and passes back into baseline region 410 at a time $t_4$. The method of the present invention provides three options for calculating time period 720 to account for this deviation. In a first embodiment, pulse generator 102 begins to accrue time for predetermined time period 720 at time $t_1$. When T-wave 717 passes outside baseline region 410 at time $t_3$, pulse generator 102 discontinues accruing time for time period 720 and zeros out the counter. Thus, when T-wave 717 passes back into baseline region 410 at time $t_4$, pulse generator 102 begins accruing time for predetermined time period 720 all over again.

In a second embodiment, pulse generator 102 accumulates time for predetermined time period 720 each time the electrical signal passes through baseline region 410. When the accumulated time totals predetermined time period 720, pulse generator 102 ends refractory period 718. In this embodiment, the time that the R-wave passes through baseline region 410 will count toward the accumulation of time by pulse generator 102. Generally, the time that it takes for the R-wave to pass through baseline region 410 is very short. This is because R-waves are commonly very steep, so the time that the R-wave is within baseline region 410 is minimal, as seen in FIG. 7. However, some patients have a characteristically flatter R-wave. This means that the time that the R-wave passes through baseline region 410 is longer. For such patients, the overall predetermined time period 720 may be extended accordingly, to account for the flatter R-wave.

In a third embodiment, pulse generator 102 accumulates the time spent in baseline region 410, however, it starts accumulation only after electrical signal has been in baseline region 410 for some minimal amount of time. This third embodiment is shown in FIG. 7. Using this embodiment, pulse generator would start accumulating at a time shortly after time $t_1$. As such, it would not include the time that the R-wave passes through baseline region 410. Then, it would accumulate the time that the electrical signal is within baseline region 410, until the total accumulated time equals predetermined time period 720. In FIG. 7, time $t_5$ indicates that the signal has settled into baseline region 410 for time period 720, and pulse generator 102 ends refractory period 718 and reinitiates sensing for a new cardiac event.

The use of minimum and maximum backup timers is also shown in FIG. 7. In particular, when R-wave 716 is sensed at time to, the microprocessor sets the minimum backup timer for a minimum predetermined period of time 721, ending at a time $t_7$ and sets the maximum backup timer for a maximum predetermined period of time 722, ending at a time $t_6$. It would be apparent to one skilled in the relevant art that the backup timers could be set to various time periods depending on the particular physiological characteristics of each individual patient. In this embodiment, minimum time period 721 is set within the range of 80 to 300 ms, and maximum time period 722 is within the range of 120 to 600 ms.

FIG. 7 shows the electrical signal resulting from an intrinsic cardiac event. In the case of a paced cardiac event, the electrical signal is longer. In this case, the maximum backup timer is set to a longer time period 722 so that the timer does not run out before the electrical activity settles into baseline region 410. Similarly, the minimum backup timer can be adjusted accordingly.

Figure 10:
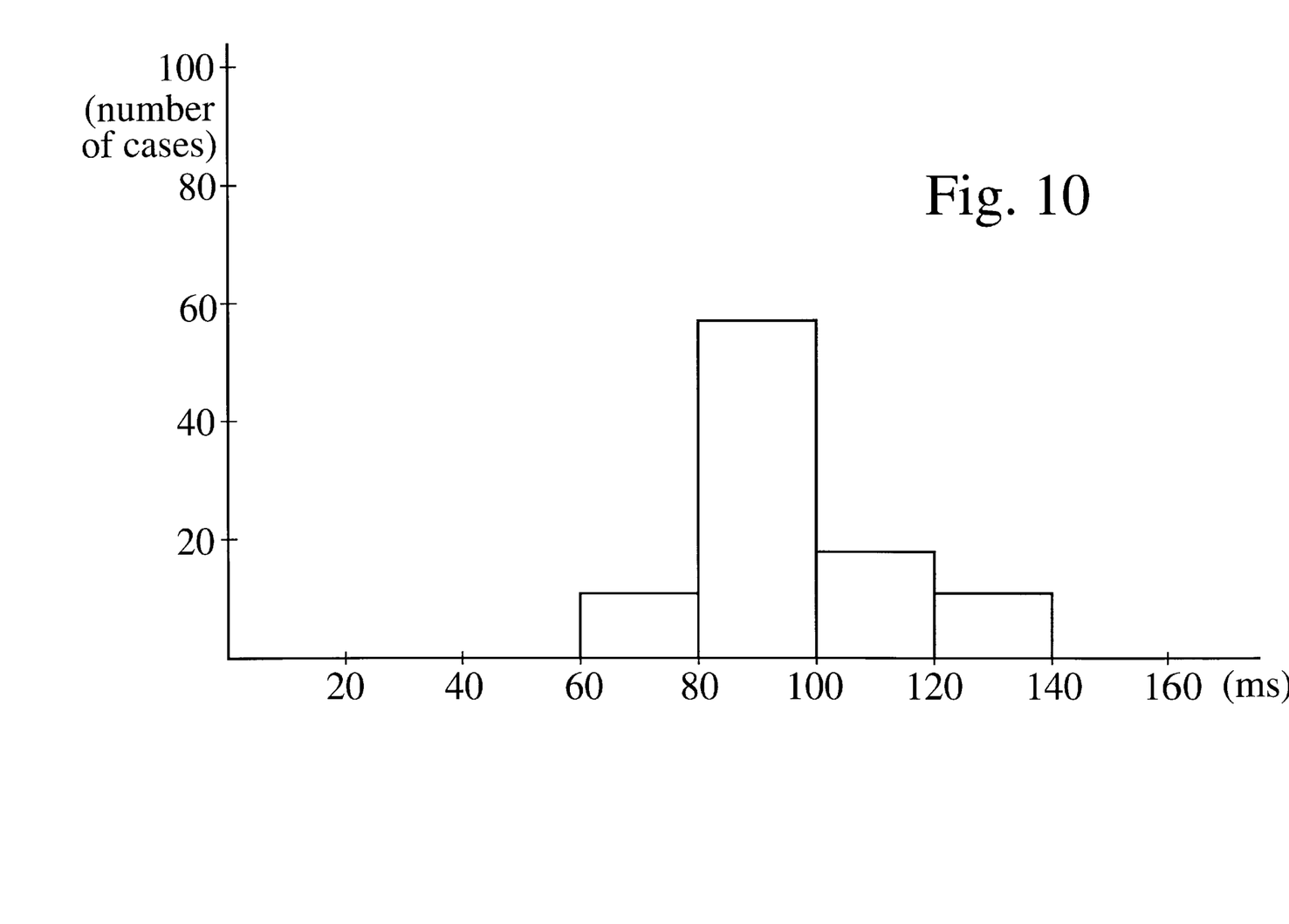
FIG. 10 is a histogram showing exemplary refractory period lengths (in milliseconds) resulting from the method of the present invention.

FIG. 10 shows a sample histogram which may be compiled to review the various actual refractory periods that result from using the method of the present invention. The x-axis of the graph of FIG. 10 represents the length of the various refractory periods in milliseconds (ms). The y-axis of the graph represents the number of cases sampled. The exemplary histogram shows that approximately 60 cases had the refractory period naturally end in the 80 to 100 ms range. The exemplary histogram further shows that approximately 20 cases had the refractory period naturally end in the 100 to 120 ms range and approximately 10 cases had the refractory period end in the 60 to 80 ms range. Assuming that the minimum backup timer is set to 60 ms, the histogram shows that no cases had the refractory period end below this minimum time period. The highest range in this graph, 120 to 140 ms, represent those cases in which the maximum backup timer caused the refractory period to end prior to the self-termination of the refractory period, i.e., the maximum time period expired before the cardiac event had settled into the baseline region for a predetermined period of time. The microprocessor of conventional pacemakers and defibrillators can be programmed to collect information relating to the refractory period. The devices can then be configured to transmit this information to an external computer or a physician as would be apparent to one skilled in the relevant art. This information could then be compiled in a graph, such as the exemplary histogram of FIG. 10, for study and use.

While the invention has been particularly shown and described with reference to preferred embodiments thereof, it will be understood by those skilled in the art that various changes in form and details may be made therein without departing from the spirit and scope of the invention.

What is claimed is:

1. A method for optimal sensing of a cardiac event, comprising the steps of:
   (a) sensing an electrical signal representative of electrical activity from a patient's heart. said electrical signal having a baseline,
   (b) registering an occurrence of said cardiac event from said electrical signal;
   (c) beginning a refractory period upon registration of said cardiac event;
   (d) providing a baseline region based on said and detecting an end of said cardiac event when said electrical activity settles into said baseline region for a predetermined period of time; and
   (e) ending said refractory period when said end of said cardiac event is detected.

2. The method of claim 1, wherein said cardiac event is registered when said electrical signal from said cardiac event crosses a predetermined sensing threshold.

3. The method of claim 1, wherein said cardiac event is registered when a pace pulse is delivered to a patient's heart.

4. The method of claim 1, wherein said cardiac event is registered when a defibrillation shock is delivered to a patient's heart.

5. The method of claim 1, wherein all of the time that said electrical activity is within said baseline region is accumulated to total said predetermined period of time for detection of said end of said cardiac event.

6. The method of claim 1, wherein said predetermined period of time is within a range of 20 to 1000 milliseconds.

7. The method of claim 1, further comprising the step of setting a maximum backup timer for a predetermined maximum time period concurrent with said step (c), and ending said refractory period after the shorter of said predetermined maximum time period as timed by said maximum backup timer or said end of said cardiac event.

8. The method of claim 7, wherein said predetermined maximum time period equals a predetermined nominal refractory period value.

9. The method of claim 7, wherein said predetermined maximum time period is within a range of 120 to 1000 milliseconds.

10. The method of claim 1, further comprising the step of setting a minimum backup timer for a predetermined minimum time period concurrent with said step (c), and ending said refractory period after the longer of said predetermined minimum time period as timed by said minimum backup timer or said end of said cardiac event.

11. A cardiac therapy device capable of monitoring a patient's heart, comprising:
   means for sensing an electrical signal having a baseline from said patient's heart and registering a cardiac event from said sensed electrical signal;
   means for beginning a refractory period upon registration of said cardiac event;
   means for providing a baseline region based on said baseline;
   means for detecting an end of said cardiac event when said electrical activity settles into said baseline region for a predetermined period of time; and
   means for ending said refractory period when said end of said cardiac event is detected.

12. The device of claim 11, further comprising:
   means for displaying to a physician a length of said refractory period.

13. The device of claim 11, wherein said cardiac event is registered when said electrical signal from said cardiac event crosses a predetermined sensing threshold.

14. The device of claim 11, wherein said cardiac event is registered when a pace pulse is delivered to a patient's heart.

15. The device of claim 11, wherein said cardiac event is registered when a defibrillation shock is delivered to a patient's heart.

16. The device of claim 11, wherein said predetermined period of time is within a range of 20 to 1000 milliseconds.

17. The device of claim 11, further comprising a maximum backup timer, wherein said timer is set for a predetermined maximum time period when said refractory period begins and said means for ending said refractory period is adapted to end said refractory period after the shorter of said predetermined maximum time period or said end of said cardiac event.

18. The device of claim 17 wherein said predetermined maximum time period is within a range of 120 to 1000 milliseconds.

19. The device of claim 11, further comprising a minimum backup timer, wherein said timer is set for a predetermined minimum time period when said refractory period begins and said means for ending said refractory period is adapted to end said refractory period after the longer of said predetermined minimum time period or said end of said cardiac event.

* * * * *